US010617597B2

(12) United States Patent
Chawan et al.

(10) Patent No.: US 10,617,597 B2
(45) Date of Patent: Apr. 14, 2020

(54) INSOLE DESIGN AND ACTUATOR PLACEMENT FOR BALANCE AND GAIT

(71) Applicant: President and Fellows of Harvard College, Cambridge, MA (US)

(72) Inventors: Arun Chawan, San Francisco, CA (US); Hani Sallum, Somerville, MA (US); Robert Wood, Cambridge, MA (US); James Niemi, Concord, MA (US); James J. Collins, Newton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 603 days.

(21) Appl. No.: 15/331,312

(22) Filed: Oct. 21, 2016

(65) Prior Publication Data

US 2017/0112712 A1 Apr. 27, 2017

Related U.S. Application Data

(60) Provisional application No. 62/245,132, filed on Oct. 22, 2015.

(51) Int. Cl.
*A61H 23/00* (2006.01)
*A43B 17/00* (2006.01)
(Continued)

(52) U.S. Cl.
CPC ............ *A61H 23/02* (2013.01); *A43B 3/0005* (2013.01); *A43B 7/146* (2013.01); *A43B 17/006* (2013.01);
(Continued)

(58) Field of Classification Search
CPC .. H04R 1/1016; H04R 1/1025; H04R 1/1041; H04R 1/1075; H04R 2420/07;
(Continued)

(56) References Cited

U.S. PATENT DOCUMENTS 5,836,899 A * 11/1998 Reilly .................. A43B 3/0005
                                              601/46
5,913,838 A *  6/1999 Reilly .................... A61H 23/02
                                              36/136
(Continued)

OTHER PUBLICATIONS

"PZ138E P-0xx Piezo Acutator User Manual, Oct. 12, 2014, PI Ceramic, Version 1.2.0, p. 55-57" (Year: 2014).*
(Continued)

*Primary Examiner* — Quang D Thanh
(74) *Attorney, Agent, or Firm* — Nixon Peabody LLP

(57) ABSTRACT

A wearable system is directed to neurological stimulation of a human foot, and includes a controller with at least one bias signal generator for outputting a driving signal. The system further includes a power source that provides electrical energy to the controller, including providing electrical energy to the bias signal generator. The system also includes a platform in the form of an insole insert of a shoe, the insole insert having a plurality of actuators positioned in a medial arch region of the foot. The plurality of actuators stimulate the medial arch region in response to receiving the driving signal from the controller. The stimulation of the plurality of actuators provides a subthreshold bias signal to target cells with a subthreshold bias signal magnitude that is below a threshold where the target cells are activated by a stimulus. The plurality of actuators is surrounded with a vibration dissipating material.

20 Claims, 8 Drawing Sheets

(51) Int. Cl.
*A43B 3/00* (2006.01)
*A61H 23/02* (2006.01)
*A43B 17/14* (2006.01)
*A43B 7/14* (2006.01)
*A61B 5/11* (2006.01)
*A61B 5/103* (2006.01)

(52) U.S. Cl.
CPC ......... *A43B 17/14* (2013.01); *A61H 23/0245* (2013.01); *A61B 5/1038* (2013.01); *A61B 5/1104* (2013.01); *A61H 2201/0165* (2013.01); *A61H 2201/164* (2013.01); *A61H 2201/165* (2013.01); *A61H 2201/5002* (2013.01); *A61H 2205/125* (2013.01)

(58) Field of Classification Search
CPC ....... A43B 3/005; A43B 17/006; A43B 17/14; A43B 7/146; A43B 3/0005; A61H 23/02; A61H 23/0245; A61H 2201/164–165; A61H 2201/168; A61H 2201/5002; A61H 2205/12; A61H 2205/125; A61H 2201/0165; A61B 5/1038; A61B 5/1104
See application file for complete search history.

(56) References Cited

U.S. PATENT DOCUMENTS

| | | | | |
|---|---|---|---|---|
| 6,195,917 | B1* | 3/2001 | Dieckhaus | A43B 7/141 36/154 |
| 7,082,704 | B2* | 8/2006 | Throneburg | A43B 7/16 36/25 R |
| 8,322,055 | B1* | 12/2012 | Saint-Cyr | A61H 23/02 36/141 |
| 8,795,210 | B2* | 8/2014 | Talish | A61H 1/005 36/141 |
| 2004/0173220 | A1* | 9/2004 | Harry | A43B 3/0005 128/892 |
| 2005/0126049 | A1* | 6/2005 | Koenig | A43B 3/0005 36/141 |
| 2007/0203435 | A1* | 8/2007 | Novak | A61B 5/1038 601/70 |
| 2008/0005936 | A1* | 1/2008 | Chiu | A43B 3/0005 36/3 B |
| 2011/0232134 | A1* | 9/2011 | Radl | A43B 3/0005 36/141 |
| 2012/0023785 | A1* | 2/2012 | Barnes | A61F 5/14 36/141 |
| 2012/0186101 | A1* | 7/2012 | Sanchez | A43B 3/0005 36/44 |

OTHER PUBLICATIONS

Centers for Disease Control and Prevention, National Center for Injury Prevention and Control, Division of Unintentional Injury Prevention. "Important Facts about Falls." retrieved from <http://www.cdc.gov/HomeandRecreationalSafety/Falls/adultfalls.html>; published 2008, last updated Sep. 20, 2016 (6 pages).
Forrest, G. et al.; "Falls on an Inpatient Rehabilitation Unit: Risk Assessment and Prevention"; Rehabil. Nurs. vol. 37, No. 2, pp. 56-61; Mar.-Apr. 2012 (6 pages).
Richardson, J.K. et al.; "Peripheral neuropathy: An often-overlooked cause of falls in the elderly"; Postgrad. Med. vol. 99, No. 6, pp. 161-172; Jun. 1996 (12 pages).
Richardson, J.K. et al.; "Peripheral Neuropathy: A True Risk Factor for Falls"; J. Gerontol. A Biol. Sci. Med. Sci., vol. 50A, No. 4, pp. M211-M215; 1995 (5 pages).
Thurman, D.J. et al.; "Practice Parameter: Assessing patients in a neurology practice for risk of falls (an evidence-based review): Report of the Quality Standards Subcommittee of the American Academy of Neurology"; Neurology, vol. 70, pp. 473-479; Feb. 5, 2008 (9 pages).
Collins, J.J. et al.; "Noise-enhanced tactile sensation"; Nature, vol. 383, p. 770; Oct. 31, 1996 (1 page).
Sejdic, E. et al.; "Necessity of noise in physiology and medicine"; Comput. Methods Programs Biomed. Aug. 2013; 111(2): pp. 459-470. doi:10.1016/j.cmpb.2013.03.014 (23 pages).
Priplata, A.A. et al.; "Vibrating insoles and balance control in elderly people"; The Lancet, vol. 362, pp. 1123-1124; Oct. 4, 2003 (2 pages).
Priplata, A.A. et al.; "Noise-Enhanced Balance Control in Patients with Diabetes and Patients with Stroke"; Ann. Neurol. 2006; 59:4-12 (9 pages).
Galica, A. et al.; "Subsensory Vibrations to the Feet Reduce Gait Variability in Elderly Fallers"; Gait Posture. Oct. 2009; 30(3): 383-387. doi.10.1016/j.gaitpost.2009.07.005 (13 pages).
Podsiadlo, D. et al.; "The Timed 'Up & Go': A Test of Basic Functional Mobility for Frail Elderly Persons"; J. Am. Geriatr. Soc. 1991—vol. 39, No. 2, pp. 142-148 (7 pages).
Wuehr, M. et al.; "Sensory loss and walking speed related factors for gait alterations in patients with peripheral neuropathy"; Gait & Posture 39 (2014) 852-858 (7 pages).
Manor, B. et al.; "Faster walking speeds increase local instability among people with peripheral neuropathy"; J. Biomech. 41 (2008) 2787-2792 (6 pages).
Dingwell, J.B. et al.; "Slower speeds in patients with diabetic neuropathy lead to improved local dynamic stability of continuous overground walking"; J. Biomech. 33 (2000) 1269-1277 (9 pages).
Bernard-Demanze, L. et al.; "Can tactile plantar stimulation improve postural control of persons with superficial plantar sensory deficit?", Aging Clin. Exp. Res. 2009, vol. 21, No. 1, pp. 1-7 (7 pages).
Lord, S.R. et al.; "Lateral stability, sensorimotor function and falls in older people"; J. Am. Geriatr. Soc. Sep. 1999, vol. 47, Issue 9, pp. 1077-1081 (8 pages).

* cited by examiner

| Characteristic | Completed Subjects (n=12) | Failed (n=27) | Vibration | Screening |
|---|---|---|---|---|
| Age (years), mean ± SD | 73.8 ± 8.1 | 79.3 ± 7.8 | | |
| 65-69, n (%) | 5 (41.7) | 4 (14.8) | | |
| 70-74, n (%) | 1 (8.3) | 5 (18.5) | | |
| 75-79, n (%) | 2 (16.7) | 1 (3.7) | | |
| 80-84, n (%) | 3 (25.0) | 9 (33.3) | | |
| 85-90, n (%) | 1 (8.3) | 8 (29.6) | | |
| Gender | | | | |
| Male, n (%) | 1 (8.3) | 8 (29.6) | | |
| Female, n (%) | 11 (91.7) | 19 (70.4) | | |
| Race | | | | |
| African-American, n (%) | 3 (25) | Not available | | |
| White, n (%) | 9 (75) | Not available | | |
| Height | | | | |
| (cm), mean ± SD | 158.1 ± 10.3 | Not available | | |
| Weight | | | | |
| (lb), mean ± SD | 147.5 ± 29.6 | Not available | | |
| BMI | | | | |
| mean ± SD | 26.7 ± 4.5 | Not available | | |
| Education | | | | |
| n>high school (%) | 9 (75) | Not available | | |

FIG. 1

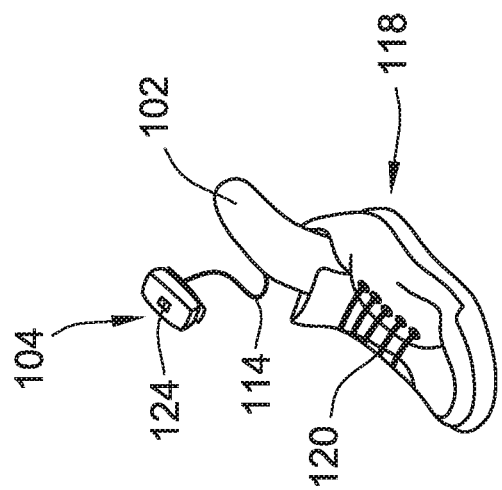
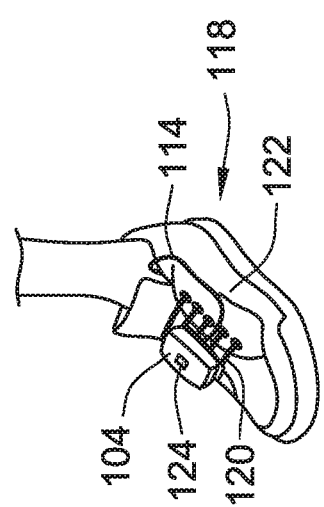
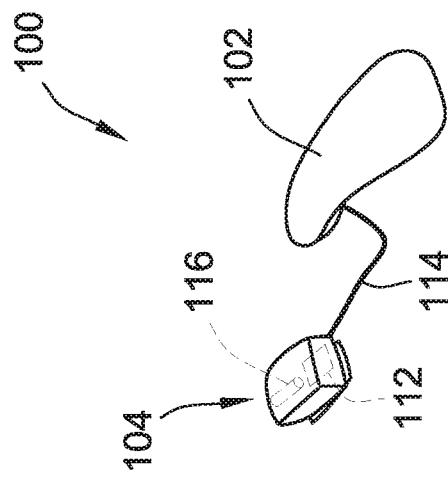
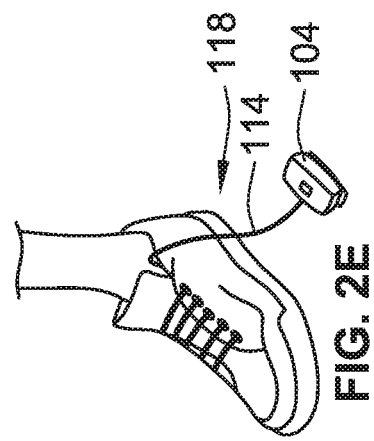
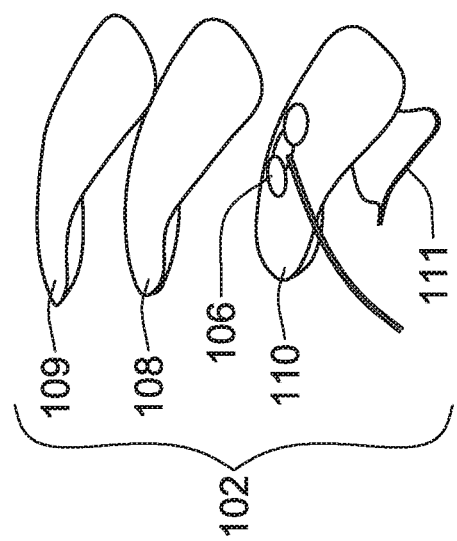
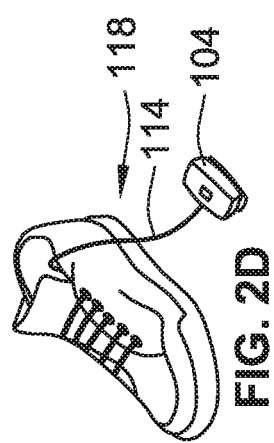

| Outcome Variable | Mean for Each Stimulation Level (CI Lower, CI Upper) | | | P value* |
|---|---|---|---|---|
| | 0% | 70% | 85% | |
| Sway speed, EO (mm/s) | 12.31 (10.45, 14.17) | 12.00 (10.14, 13.85) | 12.11 (10.25, 13.97) | 0.49 |
| Sway speed, EC (mm/s) | 19.62 (14.60, 24.65) | 18.75 (13.73, 23.77) | 19.47 (14.45, 24.50) | 0.14 |
| Area ellipse, EO (mm$^2$) | 190.8 (150.8, 230.9)$^a$ | 156.2 (116.2, 196.3)$^b$ | 159.9 (119.8, 199.9)$^b$ | <0.01 |
| Area ellipse, EC (mm$^2$) | 248.6 (196.7, 300.6)$^a$ | 217.8 (165.9, 269.8)$^b$ | 235.0 (183.0, 286.9)$^{ab}$ | 0.02 |
| ML average sway, EO (mm) | 2.63 (2.26, 2.99)$^a$ | 2.29 (1.92, 2.66)$^b$ | 2.37 (2.01, 2.74)$^b$ | 0.01 |
| ML average sway, EC (mm) | 2.83 (2.37, 3.29)$^a$ | 2.70 (2.12, 3.04)$^b$ | 2.58 (2.24, 3.16)$^b$ | 0.04 |
| AP average sway, EO (mm) | 3.90 (3.44, 4.36) | 3.76 (3.29, 4.22) | 3.63 (3.17, 4.10) | 0.11 |
| AP average sway, EC (mm) | 4.76 (4.15, 5.37) | 4.58 (3.97, 5.19) | 4.79 (4.18, 5.40) | 0.27 |

Abbreviations: EO = Eyes Open; EC = Eyes Closed; ML = Mediolateral; AP = Anteroposterior.
$^{a,b}$ Superscripts represent homogeneous groups within each row and are derived from Tukey's post hoc testing for models with a significant main effect of stimulation level. Means with different superscript are significantly different from each other. *P values reflect the effect of stimulation level on each dependent variable. No significant interactions between stimulation level and test session were observed.

FIG. 5

| Outcome Variable | Mean for Each Stimulation Level (CI Lower, CI Upper) | | | P value* |
|---|---|---|---|---|
| | 0% | 70% | 85% | |
| TUG (s) | 9.75 (9.01, 10.49)[a] | 9.44 (8.70, 10.18)[b] | 9.34 (8.60, 10.08)[b] | <0.01 |
| Gait variable means | | | | |
| Gait speed (cm/s) | 122.9 (114.1, 131.7) | 124.5 (115.7, 133.4) | 124.6 (115.8, 133.5) | 0.29 |
| Stride time, right foot (s) | 1.038 (1.008, 1.067) | 1.026 (0.996, 1.055) | 1.026 (0.997, 1.056) | 0.08 |
| Stride time, left foot (s) | 1.038 (1.009, 1.068)[a] | 1.025 (0.996, 1.055)[b] | 1.025 (0.996, 1.055)[b] | 0.04 |
| Step width, mean (cm) | 64.84 (61.51, 68.17) | 65.08 (61.74, 68.41) | 65.19 (61.86, 68.52) | 0.60 |
| Double support (s) | 0.305 (0.277, 0.334) | 0.304 (0.275, 0.333) | 0.306 (0.277, 0.334) | 0.91 |
| Gait variable CV (% of mean) | | | | |
| Stride time, right foot | 2.65 (2.43, 2.87)[a] | 2.31 (2.09, 2.54)[b] | 2.27 (2.05, 2.49)[b] | <0.01 |
| Stride time, left foot | 2.83 (2.61, 3.06)[a] | 2.32 (2.10, 2.55)[b] | 2.42 (2.20, 2.65)[b] | <0.01 |
| Step width | 3.83 (3.35, 4.30) | 3.48 (3.01, 3.95) | 3.46 (2.99, 3.93) | 0.12 |
| Double support | 8.36 (7.39, 9.33)[a] | 6.45 (5.48, 7.42)[b] | 6.49 (5.52, 7.47)[b] | <0.01 |

Abbreviations: TUG = Time Up and Go; CV = Coefficients of Variation. [a,b] Superscripts represent homogeneous groups within each row and are derived from Tukey's post hoc testing for models with a significant main effect of stimulation level. Means with different superscript are significantly different from each other. *P values reflect the effect of stimulation level on each dependent variable. No significant interactions between stimulation level and test session were observed.

FIG. 6

INSOLE DESIGN AND ACTUATOR PLACEMENT FOR BALANCE AND GAIT

CROSS-REFERENCE TO RELATED APPLICATIONS

This application claims priority to and benefit of U.S. Provisional Patent Application Ser. No. 62/245,132, filed on Oct. 22, 2015, which is hereby incorporated by reference herein in its entirety.

FIELD OF THE INVENTION

The present invention relates generally to a wearable foot system, and, more particularly, to applying a neurological stimulation to a human foot.

BACKGROUND OF THE INVENTION

Falls and mobility disorders are common, dangerous, and costly conditions among older people. Their causes are multifactorial, including impairments in vision, gait, balance, muscle strength and cognition. Loss of peripheral somatosensory function, which is common in aging, diabetes, and other causes of peripheral neuropathy, is also a risk factor for falls. Until recently, there were no proven methods to improve somatosensory function in humans.

Several non-linear biological systems, ranging from ion channels to sensory neurons, used the presence of a particular sub-threshold level of noise to enhance the detection of a weak signal. This phenomenon is known as stochastic resonance (SR), based on which subsensory vibratory noise has been applied to the feet for improving balance in healthy young and elderly subjects, and patients with diabetic neuropathy and stroke. Previous studies have suggested that SR is a potentially viable technology for improving balance and gait if it can be delivered via a shoe insole.

However, the previous studies were problematic because the vibrating tactor required a large energy source that could not be embedded into a shoe. Another problem of the previous studies was that a single baseline sensory threshold was determined through extensive testing, the amplitude of vibration having been set at 90% of this threshold.

Yet another problem of previous studies and methods was that actuator placement and insole construction focused on widely distributing vibration by placing multiple, spatially separated actuators across the insole, and on fabricating the insole from vibration propagating materials for maximizing the distribution of sensory enhancement stimulation throughout the foot surface.

Previously, it was thought that a wider distribution of stimulation was preferable for balance and gait improvement based on the greater stimulation of the field of mechanoreceptors found broadly distributed throughout the foot. As such, previous actuator positions focused on those high density regions. Furthermore, it was also previously described that rigid actuators can be placed in the arch for the purpose of isolating them from known footwear pressure points and bending planes. However, these previous placements were thought to require the use of vibration propagating structures to deliver stimulation from the arch to the areas rich in sensory mechanoreceptors.

The previous wide distribution of stimulation and placements are problematic for at least the following reasons. First, the forefoot and heel regions encounter drastically different pressures throughout the gait cycle. These pressure variations result in a constantly changing mechanical coupling between the vibration sources and the surrounding materials which leads to large changes in applied vibration levels during the gait cycle. Second, the use of vibration propagating structures leads to constructive and destructive interference of vibration patterns. This interference causes peaks and valleys across the insole resulting in difficulty setting the mechanical threshold and therapeutic vibration levels required for this therapy to be effective. In addition, vibration propagating structures are typically rigid, which makes them difficult to incorporate into insoles. Placing these materials in contact with both the skin and actuators proved to be uncomfortable. Third, the use of numerous spatially distributed actuators leads to the therapeutic level being set based on whichever region of the foot is most sensitive. Because all of the actuators are driven by the same driving signal, this can result in the stimulation being set too low.

Therefore, there is a continuing need for solving the above and other problems.

SUMMARY OF THE INVENTION

According to one aspect of the present invention, a wearable system is directed to a neurological stimulation of a human foot, and includes a controller having at least one bias signal generator for outputting a driving signal. The system further includes a power source that provides electrical energy to the controller, including providing electrical energy to the at least one bias signal generator. The system also includes a platform in the form of an insole insert of a shoe, the insole insert having a plurality of actuators positioned in a medial arch region of the foot. The plurality of actuators apply a stimulation to the medial arch region in response to receiving the driving signal from the controller. The stimulation of the plurality of actuators provides a subthreshold bias signal to target cells with a subthreshold bias signal magnitude that is below a threshold where the target cells are activated by a stimulus. The plurality of actuators is surrounded with a vibration dissipating material.

According to another aspect of the present invention, a method is directed to neurological stimulation of a human foot with a wearable system. The wearable system includes a controller with a bias signal generator, a power source, and a platform in the form of an insole insert. The insole insert has a plurality of actuators positioned in a medial arch region of a foot and is surrounded with a vibration dissipating material. The method includes providing electrical energy, via the power source, to the bias signal generator, and outputting a driving signal via the bias signal generator. In response to receiving the driving signal, a stimulation is applied to the medial arch region via the plurality of actuators. The method further includes providing a subthreshold bias signal, based on the stimulation, to target cells with a subthreshold bias signal magnitude that is below a threshold where the target cells are activated by a stimulus.

According to yet another aspect of the present invention, a wearable system is directed to neurological stimulation of a human foot, and includes a control box that encloses a controller with a bias signal generator and a power source. The bias signal generator is configured to output a driving signal, and the power source is configured to provide electrical energy to the controller. The wearable system further includes an insole insert for a shoe, the insole insert having a plurality of actuators positioned in a medial arch region. The plurality of actuators are in electrical communication with the bias signal generator and are configured to apply a stimulation to the medial arch region in response to receiving the driving signal from the bias signal generator. The insole insert further has a top layer of vibration dissipating material, the top layer being above and in contact with the plurality of actuators, and a bottom layer of vibration dissipating material, the bottom layer being below and in contact with the plurality of actuators. The stimulation of the plurality of actuators results in a subthreshold bias signal that targets cells with a subthreshold bias signal magnitude that is in the range of about 70% to about 85% of a threshold where the target cells are activated by a stimulus.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

FIG. 1 is a table with characteristics of eligible subjects and non-eligible subjects for insole vibratory stimulation study.

FIG. 2A is an exploded view showing a shoe insole.

FIG. 2B is an isometric view of the insole of FIG. 2A tethered with a control box.

FIG. 2C is an isometric view of the insole of FIG. 2A inserted into a shoe.

FIG. 2D is an isometric view of the insole and control box of FIG. 2B ready for a subject.

FIG. 2E is an isometric view of a subject having a foot placed inside the shoe of FIG. 2C.

FIG. 2F is an isometric view showing a final configuration with the control box mounted to the shoe of FIG. 2C.

FIG. 5 is a table with results of the study of FIG. 1 in reference to the effect of vibratory stimulation on balance when standing with eyes open and eyes closed.

FIG. 6 is a table with result of the study of FIG. 1 in reference to the effect of vibratory stimulation level on mobility and locomotor control.

Figure 3:
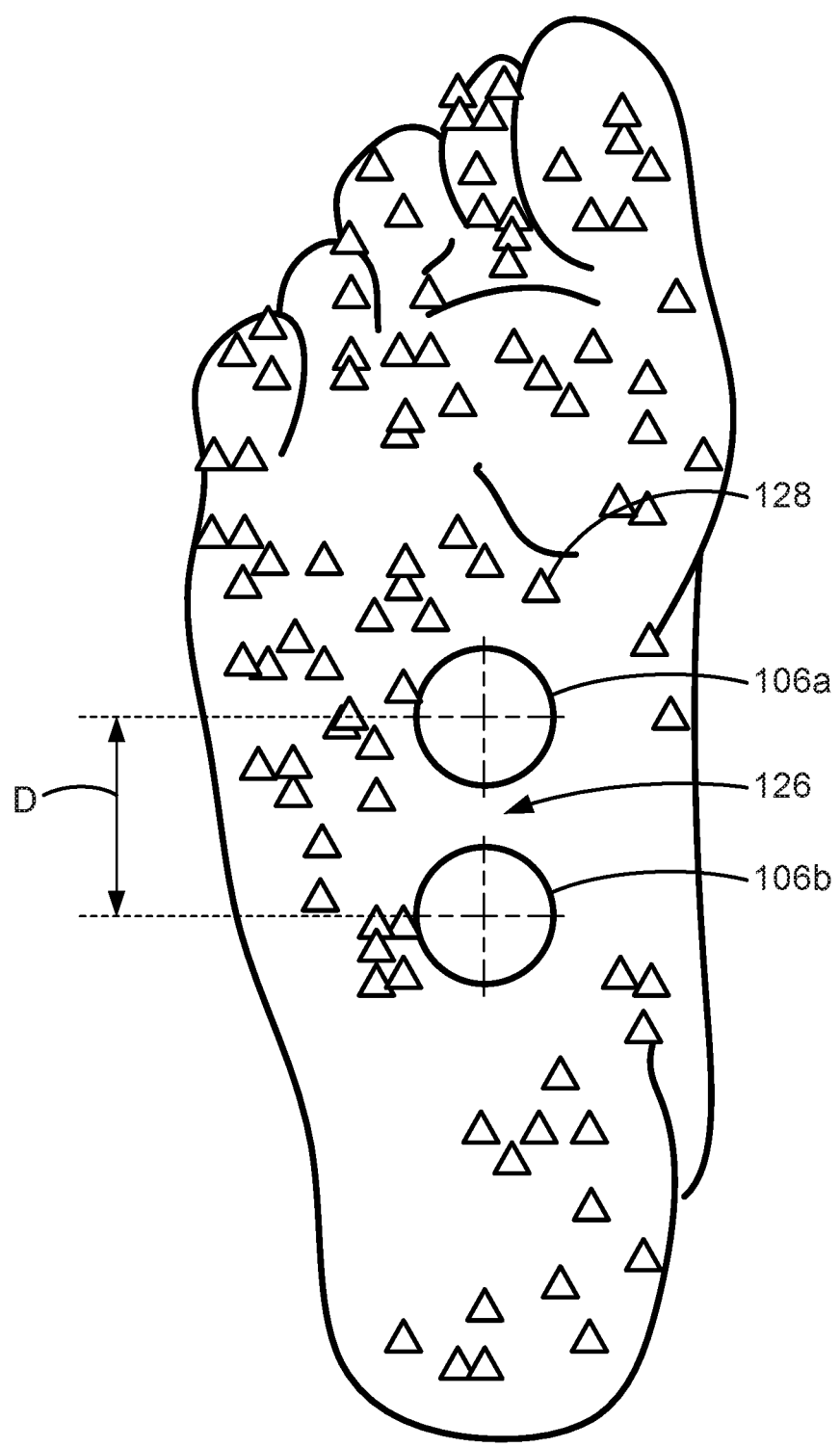
FIG. 3 is a bottom view of a foot illustrating actuator locations in areas of low mechanoreceptor density.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

In general, the description below is directed to a noise-based device, such as a shoe insole, that is effective in enhancing somatosensory function in the feet and thereby enable those with reduced plantar sole sensation to overcome associated impairments in balance and gait. In accordance with results from an exemplary randomized single-blind crossover study, which is described below in more detail, the device improves sensation, enhances balance, and reduces gait variability in humans. The study was directed to three subsensory noise stimulation levels on three separate days and included 12 healthy community-dwelling elderly volunteers of 65-90 years of age who could feel at the soles of the feet a maximum insole vibration delivered by vibratory insoles with piezoelectric actuators placed in a urethane foam insole.

More specifically, the vibratory insoles significantly improved performance on a timed up-and-go test, reduced the area of postural sway, and reduced the temporal variability of walking at both 70% and 85% of a sensory threshold, and throughout the course of a day. Vibratory sensation thresholds remained relatively stable within and across study days. Accordingly, the noise-based device of the present application improves measures of balance and gait that are associated with falls, and includes effective vibratory noise amplitudes that range from about 70% to about 85% of the sensory thresholds (which can be set once daily).

Referring to FIG. 1, a table shows characteristic of eligible subjects that completed the study and those who were excluded because they could not perceive the maximal insole vibration. The subjects were recruited from community, local senior centers, and independent living housing sites by posting flyers and giving brief presentations about the study. Potential subjects were first screened for eligibility over the phone via a brief screening questionnaire. Those who passed this initial screen were, then, evaluated for their ability to sense the vibrations delivered by the insoles. These screening visits took place at the potential subject's home or in the Clinical Research Laboratory at the Hebrew Senior-Life Institute for Aging Research. Informed consent was obtained prior to vibration screening. The subjects who were able to sense the vibration from the insoles in both feet were enrolled into the study. The 3 subsequent study visits took place at the Clinical Research Laboratory. All study visits were completed within a 14 day period with at least a day off in between. The study was approved by the Hebrew Senior-Life Institutional Review Board. The participants were fluent in English, capable of understanding and providing written informed consent, and willing to follow study instructions.

Potential participants were excluded if they had active ulcers on their feet, Parkinson's disease or other neurodegenerative conditions, or moderate to severe chronic pain in their lower extremities that interfered with standing and walking (e.g., due to arthritis, plantar fasciitis, painful peripheral neuropathy). Further exclusion criteria included potential participants that used any type of lower extremity orthotic, that could not walk unsupported around their home, that could not stand and balance unsupported for at least one minute, or that could not feel the insole vibration when the insoles were set to maximum. Other exclusion criteria included potential participants that did not feel comfortable wearing the insoles, used an Investigational New Drug within the past 30 days, were active participants in another clinical product performance study within the past 30 days, or had any condition that would make study participation inappropriate in the judgment of the Investigators.

Participants were randomized by a computerized algorithm to 3 different vibratory noise levels for the 3 days of testing. These levels were 0%, 70%, and 85% of the baseline sensory threshold measured during the first session of each day. The stimulation level remained constant for each day of testing.

Referring generally to FIGS. 2A-2F in accordance with an exemplary embodiment, a wearable system is directed to neurological stimulation of a human foot and is illustrated in the form of a vibratory insole device 100 that was used in the study. The device 100 includes a three-quarters length insole 102, a control box 104, and two piezoelectric actuators 106. The piezoelectric actuators 106, which were each 2.5 centimeters (cm) in diameter, are placed 2 cm apart in a medial arch region of each insole 102 to deliver the vibratory stimulation (see also FIG. 3 below).

Referring specifically to FIG. 2A, the insole 102 is made from urethane foam that includes a top layer 108 and a bottom layer 110 which provide double-insulation for avoiding contact with the piezoelectric actuators 106 delivering the stimulation. The insole 102 further includes a fabric top layer 109 and a bottom supporting element 111.

Referring specifically to FIG. 2B, the control box 104 includes a controller and electrical circuit components 112 and is attached to the insole 102 via a single cable 114, which provides electrical communication between the controller 112 and the actuators 106. The controller 112 is used for setting the threshold values and includes at least one bias signal generator for outputting a driving signal. A battery 116 is also located in the control box 104 and lasts approximately 8 hours on a full charge, which is sufficient for a 6-hour duration of each study visit. The battery 116 is the power source that provides electrical energy to the controller 112, including the at least one bias signal generator.

Referring specifically to FIGS. 2C-2F, when worn for the study, the insoles 102 are inserted into a subject's footwear 118 and the control box 104 with the cable 114 are secured to the shoelaces 120 or to a top area 122 of the shoe 118. Research staff ensured the participant was comfortable before beginning any study procedures. Each control box 104 has an indicator light 124 to show that the insole 102 is turned on, adequately charged, and working correctly. There were no instances of a malfunction or discomfort to the participant. The same pair of shoes 118 and insoles 102 was used for each test day for each subject. Each pair of insoles 102 was used in only one subject and they were cleaned with antiseptic spray for each day of testing.

According to one example, the piezoelectric actuators 106 are suitable for producing 3-10 microns root-mean-square (RMS) displacement while under body weight load. A custom tab and lamination process is used to firmly mount the piezoelectric actuators 106 permitting displacement while maintaining the electrical connection.

Participants were asked to bring their own sneakers and walking shoes 118 to the first study visit and the shoe 118 and insoles 102 that fit most comfortably were used for all studies. All study participants were provided with normal thickness socks to wear at all study visits to ensure a consistent sock thickness across all participants and all visits.

Referring to FIG. 3, the piezoelectric actuators include a first actuator 106a and a second actuator 106b that are placed in a foot area 126 of low mechanoreceptor density and that are surrounded in vibration absorbing foam. In this example, the area 126 of low mechanoreceptor density is the foot medial arch region. The medial arch region 126, with the lower number of mechanoreceptors 128, is a beneficial location for avoiding wide pressure fluctuations because the pressure in the arch 126 varies less during the gait cycle than in other regions. Additionally, because the average pressure in the arch 126 is lower than these other regions, power consumption for the actuators 106a, 106b is reduced.

In response to receiving the driving signal, the actuators 106a, 106b apply the stimulation to the medial arch region 126 and provide a subthreshold bias signal for targeting cells with a subthreshold bias signal magnitude that is below a threshold (e.g., about 70% to about 85% of the threshold) where the target cells are activated by a stimulus.

Another benefit of the present system is that the number of actuators, as well as a distance D between them, is minimized. Reducing the number of actuators reduces overall power consumption, and reducing the distance D between the actuators 106a, 106b reduces the sensory confusion and results in a more accurate setting of thresholds.

Yet another benefit of the present system is that the use of vibration dissipating (not vibration propagating) materials surrounding the actuators allows the use of industry standard polyurethane and ethyl vinyl acetate manufacturing processes and materials, which produces insole products already recognized and branded for their shock and vibration absorption properties. Vibration does not propagate far beyond the actuator location. The vibration reduction reduces sensory confusion, which, in turn, is helpful in setting vibration thresholds.

The ability to control frequency and amplitude separately is an important consideration in providing an appropriate noise signal for sensory enhancement. As such, from common linear actuator types, piezoelectric actuators are selected for providing the vibratory stimulation based, for example, in their thinness, durability, and efficiency.

Referring back to the study of FIG. 1, the investigators determined each participant's vibratory noise perception threshold at the start of each study visit with a computer tablet and custom software that interfaced with the insoles 102. Each foot was tested separately with the subject standing on a template that was used to assure they were in the same position for each day of testing. The amplitude of vibratory noise was automatically ramped up or down until the participant stated that they could, or could no longer, feel the stimulation. This was done in multiple stages, gradually narrowing the boundary of sensation until a reproducible threshold was determined. After the threshold values were obtained for each foot, the level of stimulation of each insole was set at 0, 70%, or 85% of the threshold value, according to the randomization order. The same thresholds were used throughout a given visit day, but threshold values were re-assessed at mid-session and at the conclusion of the study visit to compare with the daily baseline value.

Balance was assessed using a Kistler Type9286B force plate (Kistler, Amherst, N.Y.). Participants were asked to stand on a template on the force plate for a total of eight 1-minute trials, four with eyes open looking at a target "X" on the wall, and four with eyes closed. Trial order was randomized.

Gait was assessed with a 16-foot-long pressure-sensitive GAITRite® mat and data analysis software (CIR Systems, Havertown, Pa.). Participants were asked to walk across the mat ten times at his/her normal preferred walking speed.

A Timed Up and Go Test (TUG) was performed by asking the participants to sit comfortably in a chair and timing, with a stopwatch, how long it took them to stand up and walk three meters, turn around, walk back, and sit down again. Participants were asked to perform five TUG trials at each testing session.

The balance, gait, and TUG testing procedures were conducted 3 times during each study visit. A rest period of one hour occurred between each testing session. A health history questionnaire was completed and height and weight were measured for each participant during the first rest period of visit 1.

The effect of each vibratory noise level was examined on balance, gait, and TUG tasks, controlling for their within-visit test session, using repeated measures linear mixed effects regression models (SAS, PROC MIXED) and Tukey's post-hoc tests. Assessment was conducted in reference to whether attenuation of the response occurred over the course of a day by comparing the results of 3 within-day tests sessions, using similar models. Finally, the sensory thresholds were plotted for each test session and each test day, and similar models were used to assess whether there were any significant threshold changes over time. All models were adjusted for age. A p-value <0.05 was considered statistically significant.

The key outcome measures of the balance tasks were derived from the center of pressure (COP) motion using MATLAB (Mathworks, Natick, Mass.). Balance measures were calculated at each testing session for eyes open and eyes closed trials separately as an average of the four trials. Sway speed was calculated by summing the distances between consecutive COP points and dividing by the total trial time of 60 seconds. Area of the ellipse was calculated as the total area of the ellipse enclosing 95% of the COP data. Average sway in the mediolateral (ML) and anteroposterior (AP) directions were also calculated from zero-meaned data by averaging the absolute distance of excursion away from the origin in the x and y directions.

Gait variables were automatically calculated by the GAITRite® software and confirmed using an analysis program in MATLAB. Gait speed was calculated by dividing distance walked by time. Stride time was calculated separately for the right and left foot as the time between consecutive footfalls. Step width was calculated as the horizontal distance between the midpoint of each consecutive footfall. Double support time was calculated as the time within each stride that both feet were simultaneously in contact with the ground. Means and coefficients of variation (CV) were calculated using footfall data from all ten passes on the mat. CVs were calculated as the standard deviation divided by the mean multiplied by 100.

The key outcome measure of the TUG task was the total time in seconds taken to complete each trial. The average of the five TUG trials at each testing session was used for analysis.

Figure 4:
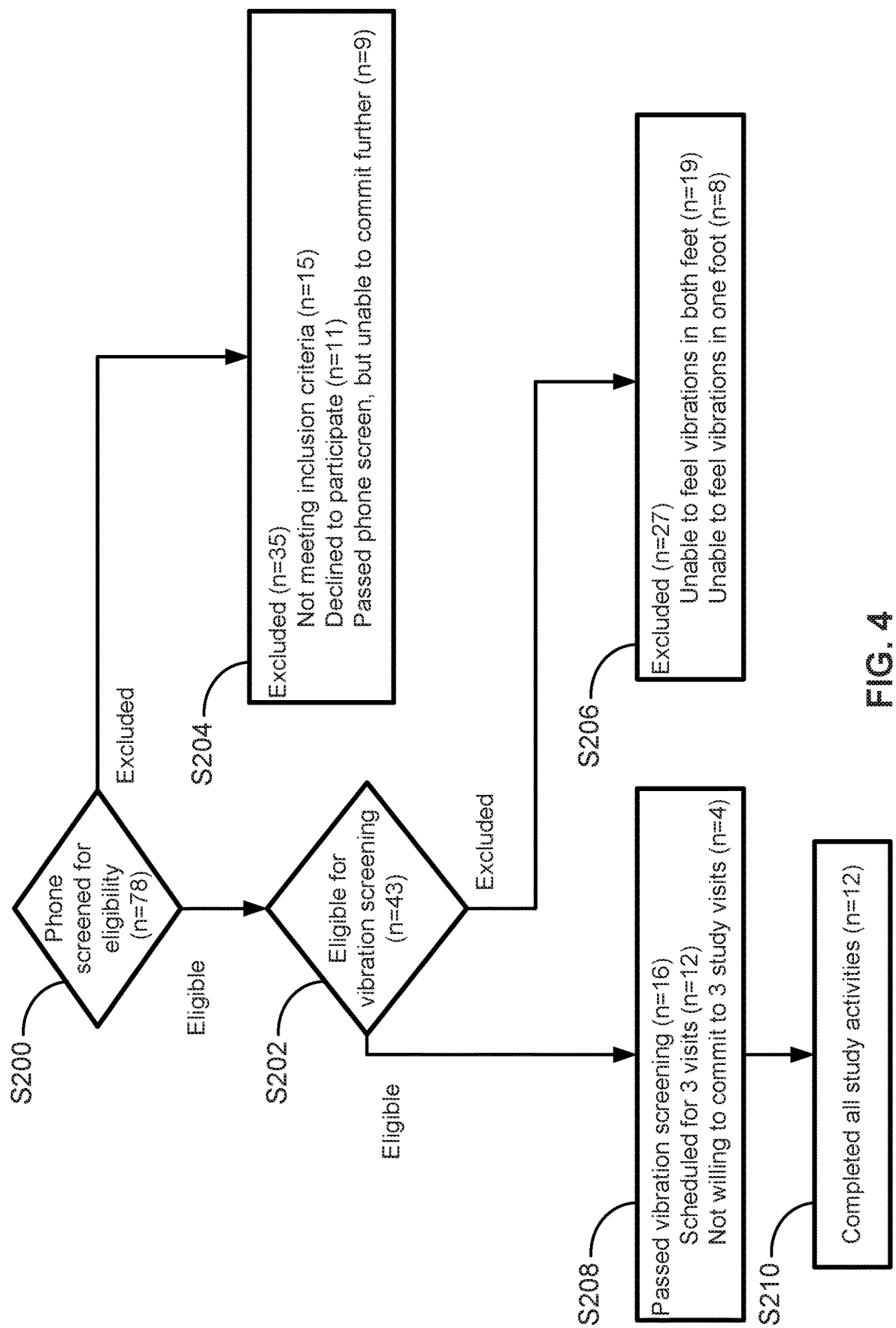
FIG. 4 is a flowchart showing a recruitment process.

Referring to FIG. 4, the process of recruitment shows that among 78 potential subjects who were screened over the phone for eligibility (S200), 43 met entry criteria (S202) and were willing to have a research assistant determine their ability to feel the vibrations delivered by the insoles. 35 of the potential subjects were excluded (S204), with 15 potential subject not meeting inclusion criteria, 11 potential subjects declining to participate, and 9 potential subjects passing phone screen but unable to commit further. From the 43 potential subjects that met the entry criteria, 27 subjects were unable to sense the vibrations in one or both feet and were excluded from the study (S206). Among the remaining 16 subjects (S208), only 12 subjects (S210) were willing to commit to three study visits. The table of FIG. 1 shows the characteristics of these 12 individuals and the characteristics of the 27 individuals who were unable to feel the vibrations at their highest amplitude. The 12 enrolled participants were younger and predominantly female compared to the other 27 individuals.

Referring to FIG. 5, a table shows the effect of vibratory noise on selected balance measures. Most of these measures improved with noise at both 70% and 85% of the sensory threshold. The average elliptical area of postural sway with eyes open and closed was reduced significantly by the vibratory noise, as was average mediolateral sway with eyes open and closed. The response was similar for both noise amplitudes, except for the area of the ellipse with eyes closed, which did not differ from sham stimulation at the 85% noise level.

Referring to FIG. 6, a table shows the results for the TUG test, walking speed, and selected gait variables. The TUG time is significantly reduced by both levels of vibratory noise. Also, the noise stimulation significantly reduces the variance in most gait measures. The coefficients of variation (CV) for stride time, step width, and double support times are significantly reduced by both levels of vibratory noise. There is a further effect on mean stride time in the right and left leg.

Figure 7B:
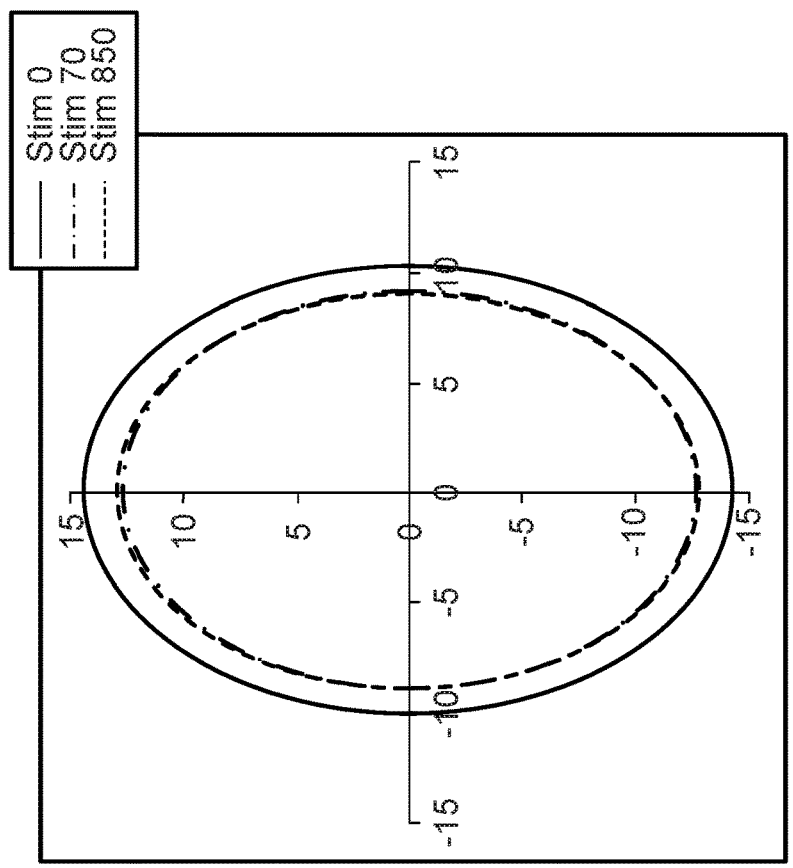
FIG. 7B is a chart illustrating the effects of subsensory vibratory stimulation for the subject of FIG. 7A with eyes closed.
Figure 7A:
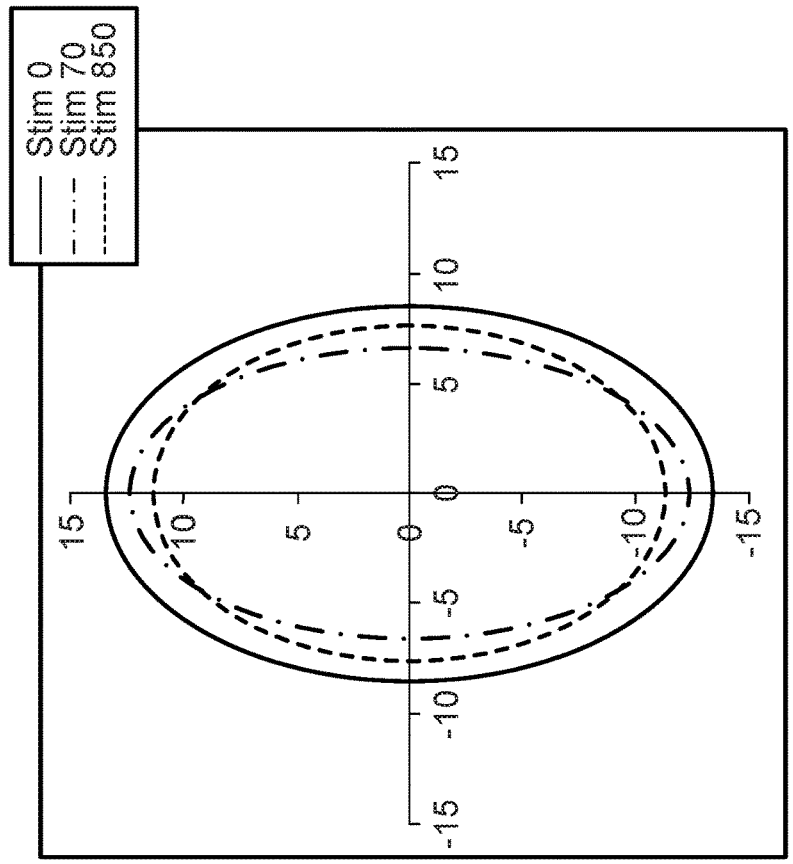
FIG. 7A is a chart illustrating effects of subsensory vibratory stimulation for a subject with eyes open.

Referring to FIGS. 7A and 7B, effects of subsensory vibratory stimulation are illustrated on an ellipse area of center of pressure for a subject. The average area of an ellipse illustrates results of a representative subject with eyes open and closed during testing at the 3 vibration levels. The ellipse encircling 95% of the center of pressure excursions during both 70% and 85% noise amplitudes is smaller than when no vibration was delivered by the insoles. There are no statistically significant effects of vibration on the magnitude of anteroposterior sway or sway speed. More specifically, in FIG. 7A, for a subject with eyes open, the area of ellipses for stimulation levels of 0%, 70%, and 85%, were 357 millimeters$^2$, 257 millimeters$^2$, and 269 millimeters$^2$, respectively. In FIG. 7B, for a subject with eyes closed, the area of ellipses for stimulation levels of 0%, 70%, and 85%, were 459 millimeters$^2$, 362 millimeters$^2$, and 361 millimeters$^2$, respectively.

Figure 8A:
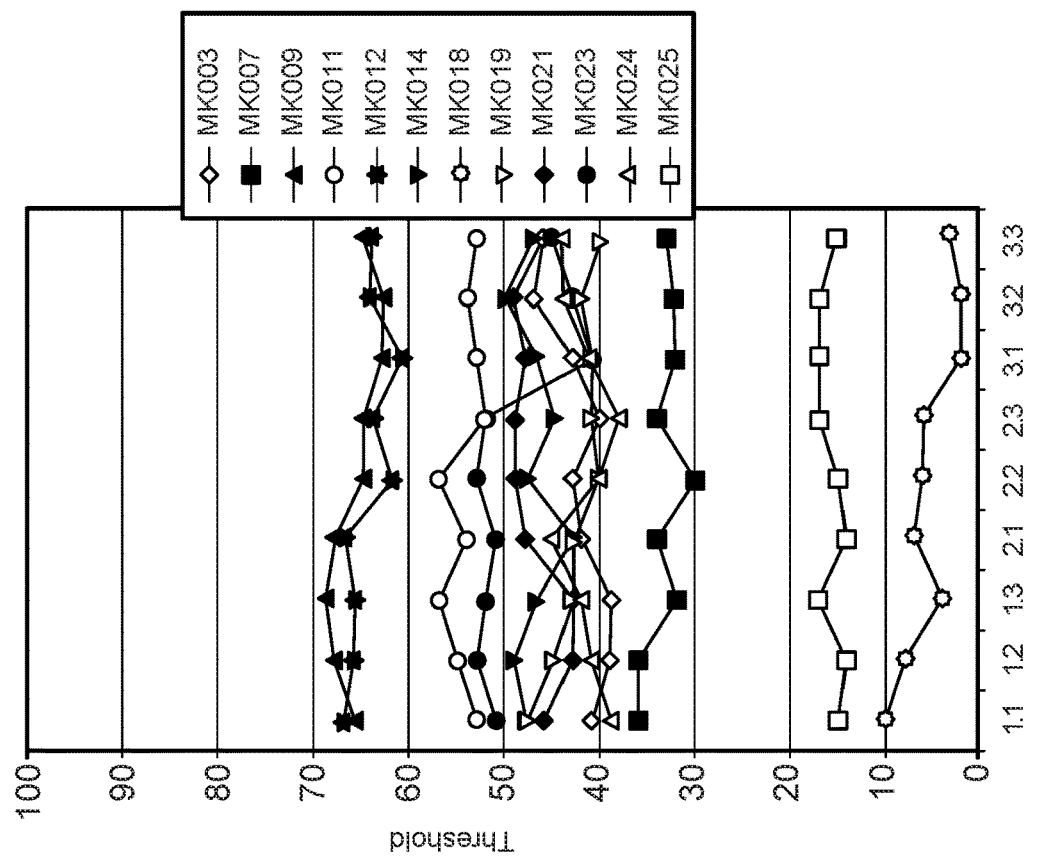
FIG. 8A is a chart illustrating left foot threshold values for each subject of the study of FIG. 1 in reference to each visit and testing session.
Figure 8B:
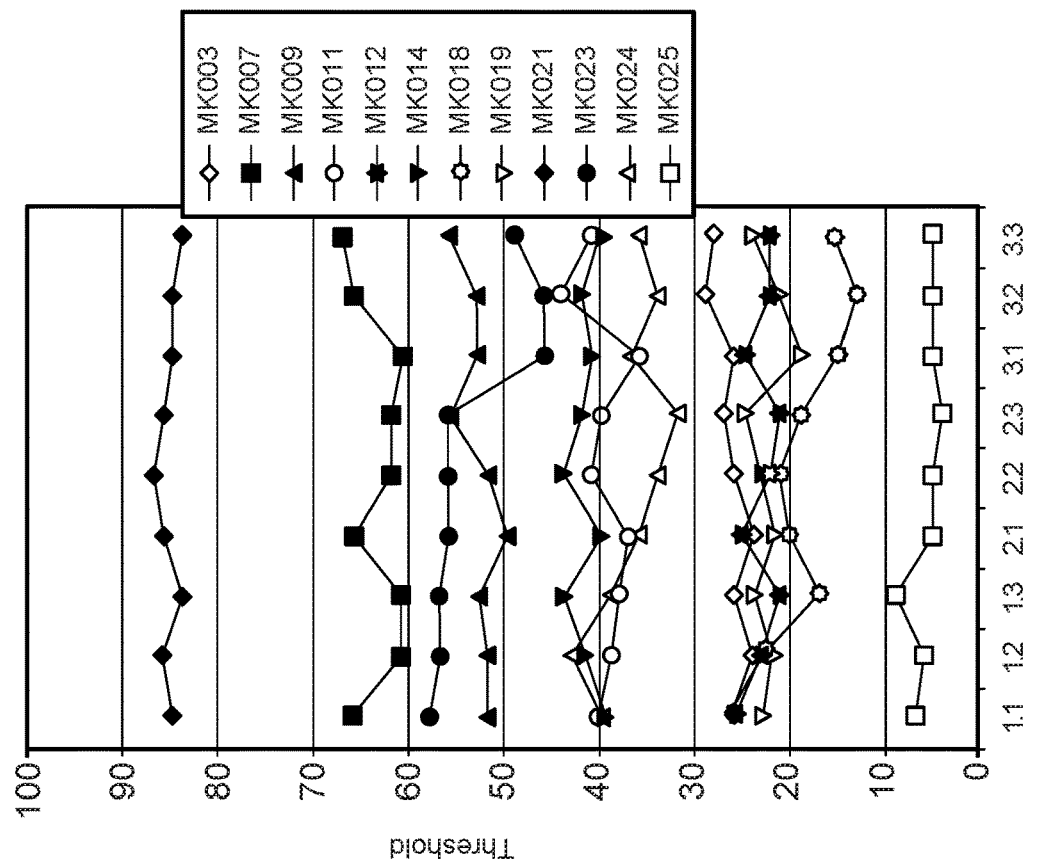
FIG. 8B is a chart illustrating right foot threshold values for each subject of the study of FIG. 1 in reference to each visit and testing session.

Referring to FIGS. 8A and 8B, threshold values for each participant's right and left foot are displayed at each visit and test session. Overall, no significant differences in thresholds occurred across test sessions within a test day, and only a marginally significant difference between test days for the left foot (P=0.05).

Referring back to FIGS. 5 and 6, no significant differences occur in the effect of the 70% and 85% vibration levels on the balance, gait, and TUG measures. Furthermore, there are no interactions between vibration level and test session for the TUG or any of the balance or gait variables, indicating that the effects of a given vibration level did not change over the course of the day. Accordingly, the results of the study demonstrate benefits of the present application's vibratory insoles, including the following:

1) the vibratory insoles of the present application significantly improve performance on the timed up-and-go test (a key outcome measure of mobility and a test that is used clinically),
2) the vibratory insoles of the present application significantly reduce the area of postural sway (i.e., COP fluctuations) when standing with eyes open and closed;
3) the vibratory insoles of the present application significantly reduce the temporal variability of walking (e.g., the coefficient of variation about the average stride, stance, step, swing, and double support times);

4) the therapeutic effect of the vibratory insoles persist throughout the course of a day;
5) vibratory sensation thresholds remain relatively stable within and across study days, reducing the frequency of setting the therapeutic level (e.g., every two weeks or less); and
6) vibratory stimulation at 70% and 85% of the sensory threshold have similar effects on standing balance, mobility, and locomotor control, which indicates that a broad stimulation range is effective and, as such, simplifying the setting of the therapeutic range because a precise setting of the therapeutic level is not required.

The results of the study further show that the application of the principle of SR to the foot sole sensory system using a new low voltage piezoelectric technology improves various measures of balance and gait that are associated with falls. Furthermore, a wider spectrum of effective vibratory noise amplitudes, than previously thought, ranges from at least about 70% to about 90% of the sensory thresholds. Such range greatly simplifies setting the therapeutic stimulation level of the insole device. The relative stability of sensory thresholds within and between days also shows that the stimulation range can be set at infrequent intervals, rather than hourly or daily.

Each of these embodiments and obvious variations thereof is contemplated as falling within the spirit and scope of the claimed invention, which is set forth in the following claims. Moreover, the present concepts expressly include any and all combinations and sub-combinations of the preceding elements and aspects.

What is claimed is:

1. A wearable system for neurological stimulation of a human foot, the system comprising:
   a controller having at least one bias signal generator for outputting a driving signal;
   a power source providing electrical energy to the controller, including the at least one bias signal generator;
   a platform in the form of an insole insert of a shoe and having a plurality of actuators positioned only in a platform medial arch region corresponding to a medial arch region of the foot, the plurality of actuators applying a stimulation to the platform medial arch region in response to receiving the driving signal from the controller, the stimulation of the plurality of actuators providing a subthreshold bias signal to target a platform cells region corresponding to cells of the foot with a subthreshold bias signal magnitude that is below a predetermined threshold value; and
   a vibration dissipating material surrounding the plurality of actuators such that the stimulation applied by the plurality of actuators is limited only to the medial arch region, the vibration dissipating material preventing the stimulation from spreading beyond the medial arch region and limiting interference of vibration patterns.

2. The system of claim 1, wherein the vibration dissipating material consists of a urethane foam.

3. The system of claim 1, wherein the plurality of actuators are piezoelectric actuators.

4. The system of claim 1, further comprising a control box in which the controller and the power source are enclosed, the control box being electrically connected to the plurality of actuators.

5. The system of claim 4, further comprising the shoe, the control box being mounted to the shoe.

6. The system of claim 1, wherein the plurality of actuators includes two piezoelectric actuators, each of the piezoelectric actuators being about 2.5 centimeters in diameter and being placed about 2 centimeters apart in the platform medial arch region.

7. The system of claim 1, wherein the vibration dissipating material is in the form of a top foam layer and a bottom foam layer, the plurality of actuators being positioned between the top foam layer and the bottom foam layer.

8. The system of claim 1, wherein the insole insert further includes a fabric layer above the vibration dissipating material and a supporting element below the vibration dissipating material.

9. The system of claim 1, wherein each of the plurality of actuators produces a displacement in the range of about 3-10 microns.

10. The system of claim 1, wherein the subthreshold bias signal magnitude is in the range of about 70% to about 85% of the predetermined threshold value.

11. A method for neurological stimulation of a human foot with a wearable system, the wearable system including a controller with a bias signal generator, a power source, and a platform in the form of an insole insert, the insole insert having a plurality of actuators positioned only in a platform medial arch region corresponding to a medial arch region of a foot and being surrounded with a vibration dissipating material, the method comprising:
    providing electrical energy, via the power source, to the bias signal generator;
    outputting a driving signal via the bias signal generator;
    in response to receiving the driving signal, applying a stimulation to the platform medial arch region via the plurality of actuators;
    providing a subthreshold bias signal, based on the stimulation, to target a platform cells region corresponding to cells of the foot with a subthreshold bias signal magnitude that is below a predetermined threshold value; and
    limiting, via the vibration dissipating material, the stimulation only to the medial arch region, the limitation of the stimulation preventing the stimulation from spreading beyond the medial arch region and limiting interference of vibration patterns.

12. The method of claim 11, wherein the controller and the power source are enclosed in a control box.

13. The method of claim 12, wherein the control box is electrically connected to the plurality of actuators.

14. The method of claim 11, further comprising displacing each of the plurality of actuators in the range of about 3-10 microns.

15. The method of claim 11, further comprising providing the subthreshold bias signal in the range of about 70% to about 85% of the predetermined threshold value.

16. A wearable system for neurological stimulation of a human foot, the system comprising:
    a control box enclosing a controller with a bias signal generator and a power source, the bias signal generator configured to output a driving signal, the power source configured to provide electrical energy to the controller; and
    an insole insert for a shoe, the insole insert including
       a plurality of actuators positioned only in a platform medial arch region corresponding to a medial arch region of the foot, the plurality of actuators being in electrical communication with the bias signal generator and configured to apply a stimulation to the platform medial arch region in response to receiving the driving signal from the bias signal generator, a top layer of vibration dissipating material, the top layer being above and in contact with the plurality of actuators, and a bottom layer of vibration dissipating material, the bottom layer being below and in contact with the plurality of actuators;

wherein the stimulation of the plurality of actuators results in a subthreshold bias signal that targets a platform cells region corresponding to cells of the foot with a subthreshold bias signal magnitude that is in the range of about 70% to about 85% of a predetermined threshold value, and wherein the top layer of vibration dissipating material and the bottom layer of vibration dissipating material limits the stimulation only to the medial arch region, the top layer of vibration dissipating material and the bottom layer of vibration dissipating material preventing the stimulation from spreading beyond the medial arch region and limiting interference of vibration patterns.

17. The wearable system of claim 16, wherein the top layer of vibration dissipating material and the bottom layer of vibration dissipating material is a urethane foam.

18. The wearable system of claim 16, wherein the plurality of actuators are piezoelectric actuators.

19. The wearable system of claim 16, wherein the plurality of actuators includes two piezoelectric actuators, each of the piezoelectric actuators being about 2.5 centimeters in diameter and being placed about 2 centimeters apart in the location corresponding to the medial arch region of the insole insert.

20. The wearable system of claim 16, wherein each of the plurality of actuators produces a displacement in the range of about 3-10 microns.

* * * * *